March 3, 1964 H. C. SWIM ETAL Plant Pat. 2,370
ROSE PLANT
Filed Feb. 25, 1963
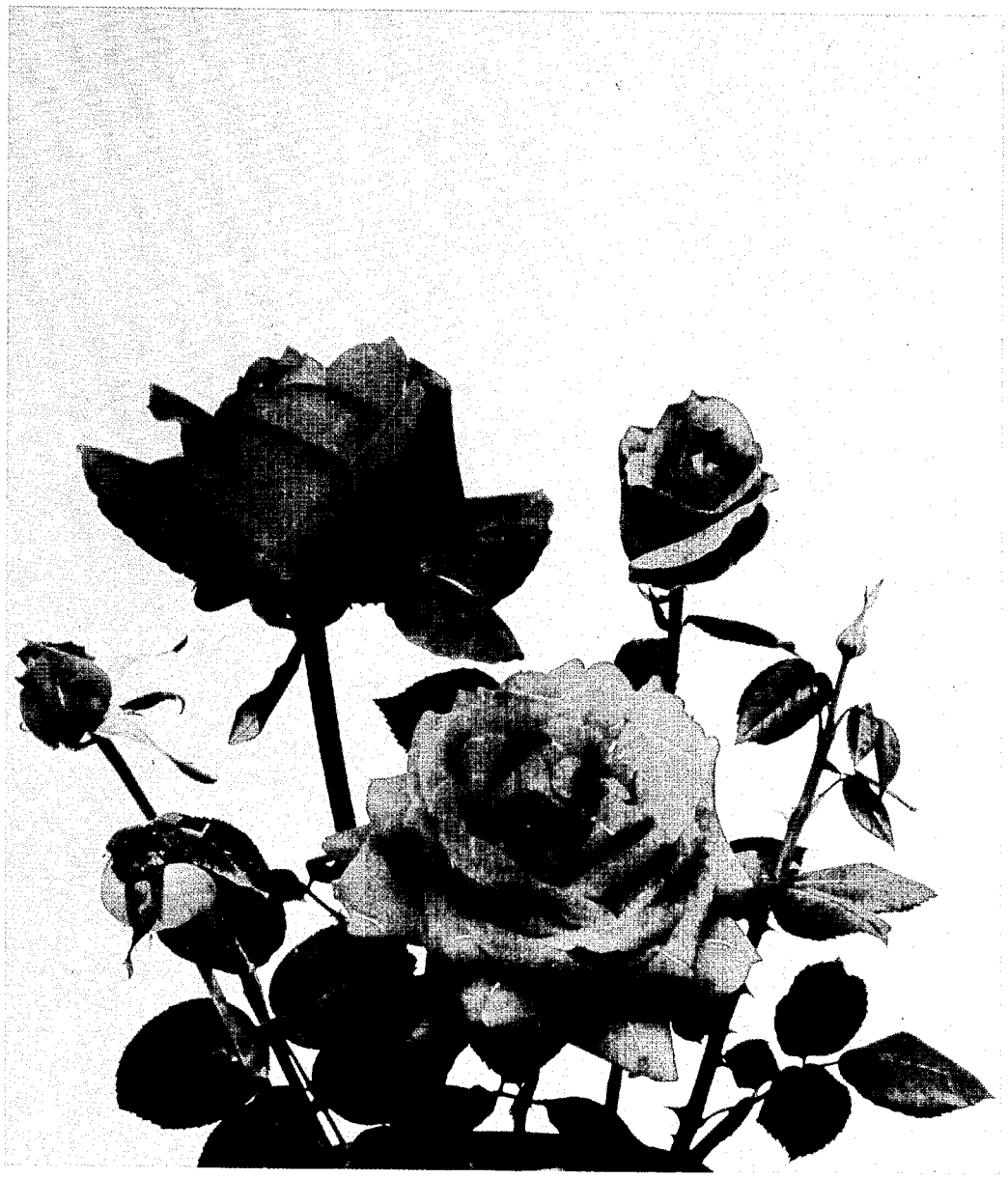
Inventors
H. C. Swim and
O. L. Weeks
By: Robb & Robb
Attorneys.

United States Patent Office

Plant Pat. 2,370
Patented Mar. 3, 1964

2,370
ROSE PLANT

Herbert C. Swim, Ontario, and O. L. Weeks, Chino, Calif., assignors, by mesne assignments, to the Conard-Pyle Company, West Grove, Pa., a corporation of Pennsylvania Filed Feb. 25, 1963, Ser. No. 260,932
1 Claim. (Cl. Plt.—20)

The present invention relates to a new and distinct variety of rose plant of the hybrid tea class, which was originated by us by crossing the variety "Chrysler Imperial" (Plant Patent No. 1,167) with the variety "Charles Mallerin" (Plant Patent No. 933).

As the result of this breeding, we have produced a new and improved rose variety having the following unique combination of characteristics which are outstanding therein and which distinguish it from its parents, as well as from all other varieties of which we are aware:

(1) Extraordinary vigorous growth which is evidenced by the fact that the new variety is among the largest in the hybrid tea class, if not actually the largest;

(2) A habit of usually producing only one flower to a stem, with the flowers being borne on exceptionally long stems growing from the base or near the base of the plant, and the stems being substantially less prickly than those of most red hybrid tea rose varieties;

(3) Exceptionally large flower size, with the flowers being the largest of any red roses of the hybrid tea class previously known to us;

(4) Good flower petalage normally numbering from 30 to 40 petals, with the petals being very large and broad;

(5) A regular arrangement of the petals in the open flowers, with a high degree of imbrication;

(6) A distinctive and attractive general color tonality of the flowers which may be generally described as dark red, but the color being lighter and brighter than the flowers of such varieties as the parent variety "Charles Mallerin," said flowers also having a white or yellow vegetative streak on the midrib of some of the outer petals of the flowers; and (7) A distinctive and pleasing flower fragrance composed of a blend of tea and damask.

In comparison with its seed parent, "Chrysler Imperial," the new variety has a much taller and more vigorous plant habit, with heavier and longer main stems, branches and flowering stems, with fewer prickles, both large and small; and bears substantially larger flowers on the average, said flowers having substantially larger individual petals, and the petals having a substantially larger breadth in proportion to their length than the flower petals of this parent variety.

As compared with the pollen parent, "Charles Mallerin," the new variety has a taller, more vigorous and more symmetrical plant habit, with many more branches, and the main stems, branches and flowering stems being of substantially larger caliper and greater length; fewer prickles, both large and small; a substantially larger average flower size; only stipitate glands on the peduncle, as distinguished from the numerous small prickles on the peduncle of this parent variety; and a definitely lighter and brighter shade of red flower color than the flowers of "Charles Mallerin."

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Half-hardy; tall; bush; outdoor; seedling; for cut flowers and for garden decoration.

Class: Hybrid tea.

Breeding: Seedling.

*Seed parent.*—"Chrysler Imperial."

*Pollen parent.*—"Charles Mallerin."

Propagation: Holds its distinguishing characteristics through succeeding propagations by budding.

*Flower*

Locality where grown and observed: Ontario, California.

Flowers borne: Usually singly and rarely more to stem; on very long and strong stems.

Quantity of bloom: From moderate to free, outdoors.

Continuity: More or less continuous during growing season.

Fragrance: Strong. Nature—a mixture of damask and tea.

Bud:

*Peduncle.*—Long; heavy; erect; stiff; almost smooth; with few stipitate glands. Color—medium green.

*Before calyx breaks.*—Size—medium for class. Form—long; pointed; with foliaceous appendages on the surface of the bud; often with foliaceous parts extending beyond the tip of the bud equal to ¾ or more of its length. Color—Dark Red, Plate 2.5R 3/7.

*As calyx breaks.*—Color—Dark Red, Plate 2.5R 3/7.

*As first petal opens.*—Size—large. Form—more or less urn-shaped. Color: outside—between Moderate Red, Plate 2.5R 4/10 and Deep Purplish Red, Plate 10RP 3/10; inside—between Strong Red, Plate 2.5R 5/12 and Moderate Red, Plate 2.5R 4/10, but brighter due to an undertone of yellow and a velvety nap.

*Opening.*—Opens up well.

Bloom:

*Size (when fully open.)*—Very large; from 4½ inches to 6 inches or more.

*Petalage.*—From double to very double; from 30 to 40 petals plus 4 to 6 petaloids; arranged regularly.

*Form.*—From cupped to high-centered at first, but becoming from flat to cupped; petals at first being loosely rolled outward and remaining loosely rolled outward at maturity.

Petals:

*Texture.*—Thick; leathery.

*Appearance.*—Inside—velvety. Outside—from shiny to satiny.

*Shape.*—Outside—very broadly orbicular, with apex having 1 or 2 notches, and often with one or two notches on lower portion of either or each lateral margin. Intermediate—from broadly obovate to broadly orbicular, with apex acute, and having 1 or 2 notches. Inside—from obovate to orbicular, with apex acute and having 1 notch or being entire.

This description of a newly opened flower was made from a rose grown outdoors during the month of December at Ontario, California:

*Color.*—Outer petal: outside surface—between Dark Red, Plate 2.5R 3/7 and Dark Purplish Red, Plate 10RP 3/10, sometimes overlaid irregularly with black or dark purple; inside surface—small area about point of attachment near Strong Orange Yellow, Plate 10YR 7/10, with remainder of petal varying in red coloration depending largely on the amount of overlay of black and Dark Purplish Red, Plate 10RP 3/10, with the basic color being between Dark Red, Plate 2.5A 3/7 and Moderate Red, Plate 2.5R 4/10; the overlay tending to follow the veinings although sometimes becoming general over the upper half of the petal, with 1 or 2, sometimes more, of the outside petals of flowers produced on the longer basal stems often containing a vegetative streak of white or pale yellow along the midrib, beginning near the base and extending toward the apex, said streak ranging from ⅛ inch to ¼ inch wide and usually more typical in flowers produced on long basal shoots, but otherwise mostly lacking or being inconspicuous. Intermediate petal: outside surface—between Moderate Red, Plate 2.5R 4/10 and Deep Purplish Red, Plate 10RP 3/10, with color being somewhat closer to the latter on the upper half and closer to the former at the base, with point of attachment Vivid Yellow, Plate 5Y 8/12; inside surface—small area at base of petal being near Strong Orange Yellow, Plate 10YR 7/10, with remainder of petal being between Dark Red, Plate 5R 3/7 and Strong Red, Plate 5R 4/12, the latter color dominating at the base and the former dominating over the remainder of the petal, but these colors appearing more vivid due to an underlying yellow color. Inner petal: outside surface—small area about point of attachment being Vivid Yellow, Plate 5Y 8/12 and extending upward as an underlay which affects the value of the red color to varying degrees over the lower half of the petal, with the lower portion of the petal being near Strong Red, Plate 5R 4/12, gradually giving way and progressing upward to between Deep Purplish Red, Plate 10RP 3/10 and Strong Purplish Red, Plate 10RP 4/12; inside surface—small area about base of petal being near Moderate Orange Yellow, Plate 10Y 8/10; progressing upward and beginning with Moderate Red, Plate 2.5R 4/10, the color gradually changes and deepens toward apex so that most of the upper portion of the petal is between Dark Red, Plate 2.5R 3/7 and Dark Purplish Red, Plate 10RP 3/10, although more vivid due to an apparent underlay of some shade of yellow.

This description was made from a rose that was open for three days outdoors during the month of December at Ontario, California:

*Color.*—Outer petal: outside surface—Vivid Yellow, Plate 5Y 8/12 at point of attachment, with remainder of petal being colored with varying shades of red beginning near point of attachment with near Strong Red, Plate 5R 4/12 and ranging through Moderate Red, Plate 2.5R 4/10 to Deep Purplish Red, Plate 10RP 3/10 near the margins; inside surface—small area about point of attachment being between Moderate Orange Yellow, Plate 10YR 8/10 and Vivid Yellow, Plate 2.5Y 8/12, influencing the red color adjacent thereto, but only briefly, with lower portion of petal being dominated by Strong Purplish Red, Plate 10RP 4/12, and upper portion being dominated by Deep Purplish Red, Plate 10RP 3/10, overlaid in varying degree with black, especially over the veins. Inner petal: outside surface—point of attachment being Vivid Yellow, Plate 5Y 8/12, with lower portion of petal being influenced by an underlay of this color, but being between Strong Red, Plate 5R 4/12 and Moderate Red, Plate 2.5R 4/10, and upper portion of petal being near Moderate Red, Plate 2.5R 4/10; inside surface—small area about point of attachment being near Vivid Yellow, Plate 2.5Y 8/12, with lower part of petal basically appearing near Strong Purplish Red, Plate 10RP 5/12, overlaid along midrib with Vivid Red, Plate 5R 5/12, and with upper portion being basically near Strong Purplish Red, Plate 10RP 4/12, but strongly influenced by an overlay of Strong Red, Plate 5R 4/12, which has slightly more intensity in the veinings and their reticulations.

*General color effect.*—Newly opened flower—basically near Moderate Red, Plate 2.5R 4/10, but overlaid strongly with Dark Red, Plate 2.5R 3/7 and variably with black. 3-days open—outer portion basically Moderate Red, Plate 2.5R 4/10, changing in various degree to Deep Purplish Red, Plate 10RP 3/10, with center of flower being between Strong Red, Plate 5R 4/12 and Moderate Red, Plate 2.5R 4/10.

*Behavior.*—Drop off cleanly, except for occasional petaloids.

*Flower longevity.*—On bush in garden—4 or 5 days in December. Cut roses grown outdoors and kept at living-room temperatures—3 or 4 days in December.

*Reproductive Organs*

Stamens: Medium quantity; arranged more or less irregularly, partly about pistils and partly mixed with petaloids.

Filaments: Medium long; most with anthers. Color—yellow.

Anthers: Small for class; open at various times. Color—yellow.

Pollen: From sparse to moderate quantity. Color—yellow.

Pistils: Medium quantity.

Styles: Uneven; from medium length to long; from thin to medium caliper; arranged very irregularly, being twisted, bent, matted, etc.

Stigma: Color—yellow.

Ovaries: Most enclosed in, but some protruding from calyx.

Hips: Usually very short; flat; globular; somtimes with a conspicuous neck; moderately smooth; walls thick and fleshy. Color—yellow, with some reddish markings and becoming near orange color when mature.

Sepals: Permanent; moderately long; more or less straight and spear-shaped, but sometimes curled.

Seeds: From few to many; medium size for class; usually from 5 to 18 seeds per hip.

*Plant*

Foliage:

*Leaves.*—Compound of 3, 5 or 7 leaflets; normal quantity; large size; moderately heavy; leathery; non-glossy.

*Leaflets.*—Shape—elliptic, with apex from acute to acuminate. Base—from round to cuneate. Margin—both simply and doubly serrate.

*Color.*—Mature: upper surface—dark green; under surface—gray-green. Young: upper surface—basically yellowish green, overlaid with dark purplish red, especially on veins; under surface—reddish purple reticulations almost completely dominate basic yellow-green.

*Rachis (the supporting stem of the compound leaf).*—Medium weight. Upper side—grooved; edges lined with stipitate glands. Under side—sparsely prickly.

*Stipules.*—Medium length; mostly adnate to petiole; narrow; with short points turning out at an angle of more than 45°.

*Disease resistance.*—Medium resistance to powdery mildew, as determined by comparison with other red rose varieties grown under comparable conditions at Ontario, California.

Growth:

*Habit.*—Very tall; bushy; upright; much-branched.

*Growth.*—Very vigorous.

*Canes.*—Heavy.

*Main stems.*—Color—yellow green. Large prickles—several; medium length; straight; with short, broad base; color—gray-brown. Small prickles—several; color—gray-brown. Hairs—few; color—brown.

*Branches.*—Color—gray-green. Large prickles —several; medium length; straight; with short, broad base; color—brown. Small prickles—several; color—brown. Hairs—few; color—brown.

*New shoots.*—Color—purplish red. Large prickles—several; medium length; straight; with short, broad base; color—purplish red. Small prickles—several; color—reddish purple. Hairs—few; color—reddish purple.

We claim:

A new and distinct variety of rose plant of the hybrid tea class, substantially as herein shown and described, characterized particularly as to novelty by the unique combination of an extraordinarily vigorous and large habit of growth, a habit of usually bearing flowers singly on long stems, with fewer prickles than the average red hybrid tea rose varieties, exceptionally large flower size, good flower petalage, with the individual petals being very large and broad, regular arrangement of the petals in the open flowers, with a high degree of imbrication, a distinctive and attractive dark red general color tonality of the flowers, said flowers having a white or yellow vegetative streak on the midrib of some of the outer petals, and a distinctive and strong flower fragrance characterized by a blend of tea and damask.

No references cited.